(12) United States Patent
Hopman et al.

(10) Patent No.: US 10,258,347 B2
(45) Date of Patent: Apr. 16, 2019

(54) EXTREMITY TOURNIQUET

(71) Applicant: The Seaberg Company, Inc., Wilsonville, OR (US)

(72) Inventors: Lance D. Hopman, Tigard, OR (US); Eric E. Batdorf, Oregon City, OR (US)

(73) Assignee: THE SEABERG COMPANY, INC., Wilsonville, OR (US)

( * ) Notice: Subject to any disclaimer, the term of this patent is extended or adjusted under 35 U.S.C. 154(b) by 0 days.

(21) Appl. No.: 14/324,672

(22) Filed: Jul. 7, 2014

(65) Prior Publication Data

US 2015/0216536 A1 Aug. 6, 2015

Related U.S. Application Data

(60) Provisional application No. 61/935,566, filed on Feb. 4, 2014.

(51) Int. Cl.
*A61B 17/132* (2006.01)
*A61B 17/135* (2006.01)

(52) U.S. Cl.
CPC ........ *A61B 17/1322* (2013.01); *A61B 17/135* (2013.01); *A61B 17/1327* (2013.01)

(58) Field of Classification Search
CPC ... A61B 17/12; A61B 17/132; A61B 17/1322; A61B 17/1325; A61B 17/1327; A61B 17/135; A61B 17/1355; A61B 2017/12004; A61F 5/058; A61F 5/05883; A61F 5/05825; G01L 5/04; G01L 5/047; G01L 5/06
See application file for complete search history.

(56) References Cited

U.S. PATENT DOCUMENTS

| | | | |
|---|---|---|---|
| 1,281,653 | A | 10/1918 | Plummer |
| 1,679,978 | A | 8/1928 | Konwiser |
| 2,113,534 | A | 4/1938 | Brown |
| 2,344,021 | A | 3/1944 | Bouziane |
| 2,387,428 | A | 10/1945 | Brothers |
| 2,554,337 | A | 5/1951 | Lampert |
| 3,171,410 | A | 3/1965 | Towle, Jr. et al. |
| 3,594,872 | A | 7/1971 | Kulwin et al. |
| 3,933,150 | A | 1/1976 | Kaplan et al. |

(Continued)

FOREIGN PATENT DOCUMENTS

| | | |
|---|---|---|
| DE | 20300739 | 5/2003 |
| EP | 0462088 | 12/1991 |

(Continued)

OTHER PUBLICATIONS

US Patent and Trademark Office as ISA, International Search Report issued in PCT/US2015/012296, dated May 4, 2015, 2 pages, USPTO, Alexandria, VA.

(Continued)

*Primary Examiner* — Robert A Lynch
(74) *Attorney, Agent, or Firm* — Schwabe, Williamson & Wyatt, P.C.

(57) ABSTRACT

A tourniquet for application to a patient's limb in an emergency situation, and a method for application of the tourniquet. The tourniquet includes a tension-sensing mechanism used to establish a baseline tension in a loop around an injured limb, and a tension-increasing mechanism to tighten the tourniquet as required beyond the baseline tension.

12 Claims, 11 Drawing Sheets

(56) References Cited

U.S. PATENT DOCUMENTS

| | | |
|---|---|---|
| 4,049,854 A | 9/1977 | Casey et al. |
| 4,175,562 A | 11/1979 | Honan |
| 4,233,980 A | 11/1980 | McRae et al. |
| 4,390,014 A | 6/1983 | Forman |
| 4,459,979 A | 7/1984 | Lewis, Jr. |
| 4,545,370 A | 10/1985 | Welsh |
| 4,577,622 A | 3/1986 | Jennings |
| 4,580,555 A | 4/1986 | Coppess |
| 4,715,364 A | 12/1987 | Noguchi |
| 4,928,674 A | 5/1990 | Halperin et al. |
| 4,964,401 A | 10/1990 | Taigen |
| 4,982,884 A | 1/1991 | Wise |
| 4,991,573 A | 2/1991 | Miller |
| 5,086,759 A | 2/1992 | Buddingh |
| 5,234,459 A | 8/1993 | Lee |
| 5,307,521 A | 5/1994 | Davis |
| 5,307,811 A | 5/1994 | Sigwart et al. |
| 5,338,239 A | 8/1994 | Cleaveland |
| 5,383,893 A | 1/1995 | Daneshvar |
| 5,383,920 A | 1/1995 | Sikes |
| 5,403,266 A | 4/1995 | Bragg et al. |
| 5,407,422 A | 4/1995 | Matthijs et al. |
| 5,433,724 A | 7/1995 | Kawasaki et al. |
| 5,486,194 A | 1/1996 | Kawasaki et al. |
| 5,489,260 A | 2/1996 | Striano |
| 5,500,959 A | 3/1996 | Yewer, Jr. |
| 5,515,867 A | 5/1996 | Lamb |
| 5,529,229 A | 6/1996 | Fier |
| 5,542,427 A | 8/1996 | Akerfeldt |
| 5,551,085 A | 9/1996 | Leighton |
| 5,643,315 A | 7/1997 | Daneshvar |
| 5,695,453 A | 12/1997 | Neal |
| 5,707,177 A | 1/1998 | Lehrer et al. |
| 5,741,295 A | 4/1998 | McEwen |
| 5,743,864 A | 7/1998 | Baldwin, II |
| 5,785,671 A | 7/1998 | Striano |
| 5,788,685 A | 8/1998 | Islava |
| 5,792,173 A | 8/1998 | Breen et al. |
| 5,799,650 A | 9/1998 | Harris |
| 5,830,168 A | 11/1998 | Finnell et al. |
| 5,893,368 A | 4/1999 | Sugerman |
| 5,968,072 A | 10/1999 | Hite et al. |
| 5,997,564 A | 12/1999 | Shehata et al. |
| 6,007,559 A | 12/1999 | Arkans |
| 6,053,883 A | 4/2000 | Schiek, Sr. |
| 6,065,166 A | 5/2000 | Sharrock et al. |
| 6,066,109 A | 5/2000 | Buser et al. |
| 6,165,147 A | 12/2000 | Morrow |
| 6,240,923 B1 | 6/2001 | Barrick |
| 6,264,673 B1 | 7/2001 | Egnelov |
| 6,331,170 B1 | 12/2001 | Ordway |
| 6,352,074 B1 | 3/2002 | Okada |
| 6,503,217 B1 | 1/2003 | Gibbs et al. |
| 6,503,266 B1 | 1/2003 | Sjogren et al. |
| 6,506,217 B1 | 1/2003 | Gibbs et al. |
| 6,554,784 B1 | 4/2003 | Krieg et al. |
| 6,610,022 B1 | 8/2003 | Ashbaugh et al. |
| 6,616,620 B2 | 9/2003 | Sherman et al. |
| 6,626,856 B2 | 9/2003 | Manoach |
| 6,676,620 B2 | 1/2004 | Schwenn et al. |
| 6,884,254 B2 | 4/2005 | Brooks |
| 6,899,720 B1 | 5/2005 | McMillan |
| 6,939,314 B2 | 9/2005 | Hall |
| 6,998,510 B2 | 2/2006 | Buckman et al. |
| 7,008,389 B2 | 3/2006 | Krieg et al. |
| 7,094,213 B1 | 8/2006 | Cook |
| 7,329,792 B2 | 2/2008 | Buckman et al. |
| 7,473,235 B2 | 1/2009 | Schwenn et al. |
| 7,574,761 B2 | 8/2009 | Davis |
| 7,677,605 B2 | 3/2010 | Cook |
| 7,776,064 B2 | 8/2010 | Jennifer et al. |
| 7,776,067 B2 | 8/2010 | Johnson |
| 7,842,067 B2 | 11/2010 | Esposito |
| 7,892,253 B2 | 2/2011 | Esposito |
| 7,931,607 B2 | 4/2011 | Biondo et al. |
| 7,947,061 B1 | 5/2011 | Reis |
| 8,007,453 B2 | 8/2011 | Richardson |
| 8,142,378 B2 | 3/2012 | Reis et al. |
| 8,192,383 B2 | 6/2012 | Polliack et al. |
| 8,926,536 B2 | 1/2015 | Hopman et al. |
| 9,028,435 B2 | 5/2015 | Hopman et al. |
| 2001/0053884 A1 | 12/2001 | Krieg et al. |
| 2002/0068890 A1 | 6/2002 | Schwenn et al. |
| 2002/0144343 A1 | 10/2002 | Kuiper et al. |
| 2002/0169401 A1 | 11/2002 | Walpin |
| 2003/0144343 A1 | 7/2003 | Heitsch |
| 2003/0176825 A1 | 9/2003 | Yavnai |
| 2003/0176828 A1 | 9/2003 | Buckman et al. |
| 2004/0039321 A1 | 2/2004 | Krieg et al. |
| 2004/0267292 A1 | 12/2004 | Byrum et al. |
| 2005/0113866 A1 | 5/2005 | Heinz et al. |
| 2005/0267518 A1 | 12/2005 | Wright et al. |
| 2005/0273134 A1 | 12/2005 | Esposito |
| 2005/0283102 A1 | 12/2005 | Schwenn et al. |
| 2006/0135898 A1 | 6/2006 | Richardson |
| 2006/0206992 A1 | 9/2006 | Godshaw et al. |
| 2007/0022577 A1 | 2/2007 | Funo |
| 2007/0117479 A1 | 5/2007 | Weinel et al. |
| 2007/0130735 A1 | 6/2007 | Diamond |
| 2007/0282230 A1 | 12/2007 | Valderrabano et al. |
| 2008/0004555 A1 | 1/2008 | Reis et al. |
| 2008/0251087 A1 | 10/2008 | Richardson |
| 2008/0281351 A1 | 11/2008 | Croushom et al. |
| 2009/0300888 A1 | 12/2009 | Shiue |
| 2010/0071173 A1 | 3/2010 | Hortnagl |
| 2010/0100120 A1 | 4/2010 | Perkins et al. |
| 2010/0152770 A1 | 6/2010 | Spencer |
| 2010/0179586 A1 | 7/2010 | Ward et al. |
| 2011/0034845 A1 | 2/2011 | Polliack et al. |
| 2011/0130739 A1 | 6/2011 | Fitzpatrick et al. |
| 2012/0071917 A1 | 3/2012 | McDonald et al. |
| 2012/0245500 A1* | 9/2012 | Polliack .............. A61F 5/05883 602/18 |
| 2013/0110019 A1 | 5/2013 | Hopman et al. |
| 2013/0324898 A1 | 12/2013 | Polliack et al. |
| 2014/0155797 A1 | 6/2014 | Hopman et al. |
| 2015/0359542 A1 | 12/2015 | Steinbaugh et al. |
| 2017/0035440 A1 | 2/2017 | Hopman et al. |

FOREIGN PATENT DOCUMENTS

| | | |
|---|---|---|
| EP | 2461772 | 12/2015 |
| FR | 838543 A | 3/1939 |
| GB | 2523504 A | 8/2015 |
| KR | 01-1990-0005852 B1 | 8/1990 |
| WO | 1994005221 | 3/1994 |
| WO | 1997002783 | 1/1997 |
| WO | 2000045756 A1 | 8/2000 |
| WO | 2001060290 | 8/2001 |
| WO | 2001089433 A1 | 11/2001 |
| WO | 2003075743 A2 | 9/2003 |
| WO | 2006116413 A2 | 11/2006 |
| WO | 2011016824 | 2/2011 |
| WO | 2011016824 A3 | 2/2011 |
| WO | 2013025546 A1 | 2/2013 |
| WO | 2014089243 | 6/2014 |
| WO | 2015119774 | 8/2015 |
| WO | 2018075644 | 4/2018 |

OTHER PUBLICATIONS

US Patent and Trademark Office as ISA, Written Opinion of the International Searching Authority issued in PCT/US2015/012296, dated May 4, 2015, 6 pages, USPTO, Alexandria, VA.

AMBU—Photos of Cervical Collar, prior to May 2012, 4 pages.

Pyng Medical, "T-Pod Pelvic Stabilization Device" Instruction Sheet, PM-032b, prior to May 2012, Richmond, British Columbia, Canada, 1 page.

Blackbourne et al., "Joseph Lister, Noncompressible Arterial Hemorrhage, and the Next Generation of Tourniquets'?", vol. No. Jan.-Mar. 2008, Issue No. PB 8-08-1/2/3, AMEDD Journal, The

(56) References Cited

OTHER PUBLICATIONS

United States Army Medical Department, Fort Sam Houston, Texas, 6 pages.
Kinzel, "Development of a Field Packable Junctional Tourniquet", Jan. 21, 2011, MilTech, Bozeman, Montana, 16 pages.
Kragh, Jr. et al., "New Tourniquet Device Concepts for Battlefield Hemorrhage Control", Issue No. Apr.-Jun. 2011, AMEDD Journal, The Army Medical Department Journal, pp. 38-47.
European Patent Office, "Extended European Search Report" for EP App. No. 15746775.4, dated Sep. 21, 2017, Munich, Germany, 9 pages.
US Patent and Trademark Office, "International Search Report and Written Opinion", for PCT App. No. PCT/US2013/073191, dated Apr. 21, 2014, Alexandria, Virginia, 10 pages.
US Patent and Trademark Office, "International Search Report and Written Opinion", for PCT App. No. PCT/US2015/012296, dated May 4, 2015, Alexandria, Virginia, 10 pages.
The International Bureau of WIPO, "Preliminary Report on Patentability" for PCT App. No. PCT/US2015/012296, dated Aug. 18, 2016, Geneva, Switzerland, 8 pages.
Korean Intellectual Property Office, "International Search Report and Written Opinion", for PCT App. No. PCT/US2010/001682, dated Mar. 15, 2011,Daejeon, Republic of Korea, 11 pages.
US Patent and Trademark Office, "International Search Report and Written Opinion", for PCT App. No. PCT/US2012/050437, dated Dec. 31, 2012, Alexandria, Virginia, 17 pages.
European Patent Office, "Extended European Search Report" for EP App. No. 10806730.7, dated Jan. 10, 2013, Munich, Germany, 5 pages.
US Patent and Trademark Office, "International Search Report and Written Opinion", for PCT App. No. PCT/US2014/016305, dated May 30, 2014, Alexandria, Virginia, 17 pages.
The International Bureau of WIPO, "Preliminary Report on Patentability" for PCT App. No. PCT/US2012/050437, dated Feb. 27, 2014, Geneva, Switzerland, 13 pages.
The International Bureau of WIPO, "Preliminary Report on Patentability" for PCT App. No. PCT/US2014/016305, dated Jun. 25, 2015, Geneva, Switzerland, 9 pages.
The International Bureau of WIPO, "Preliminary Report on Patentability" for PCT App. No. PCT/US2010/001682, dated Feb. 7, 2012, Geneva, Switzerland, 5 pages.

\* cited by examiner

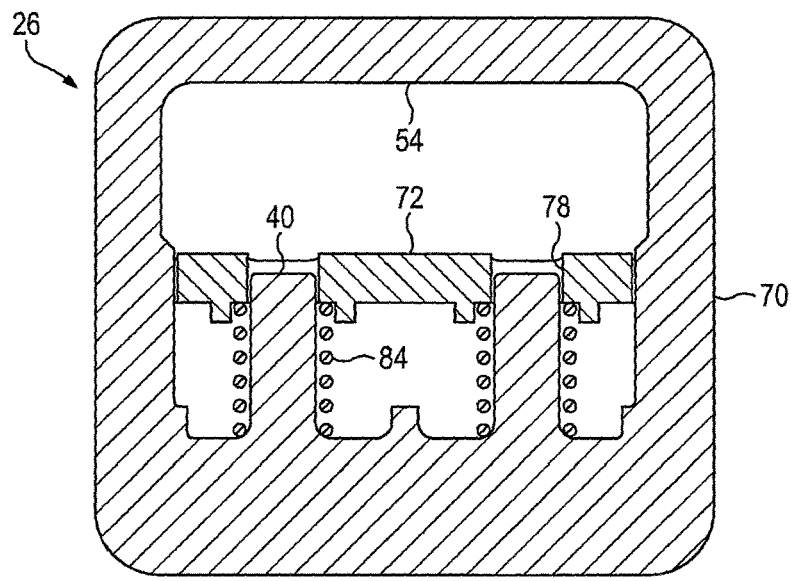
FIG. 8
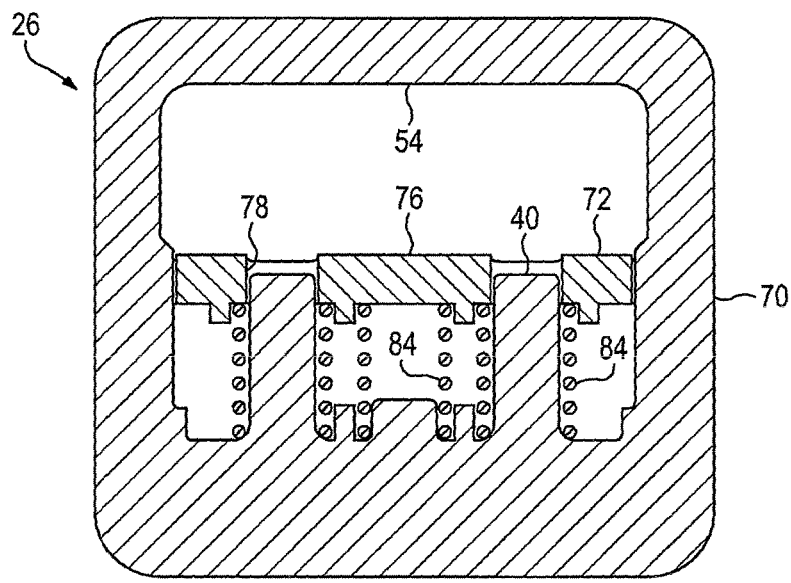
FIG. 9
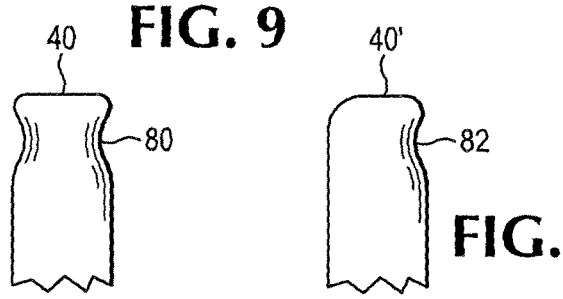
FIG. 10   FIG. 11

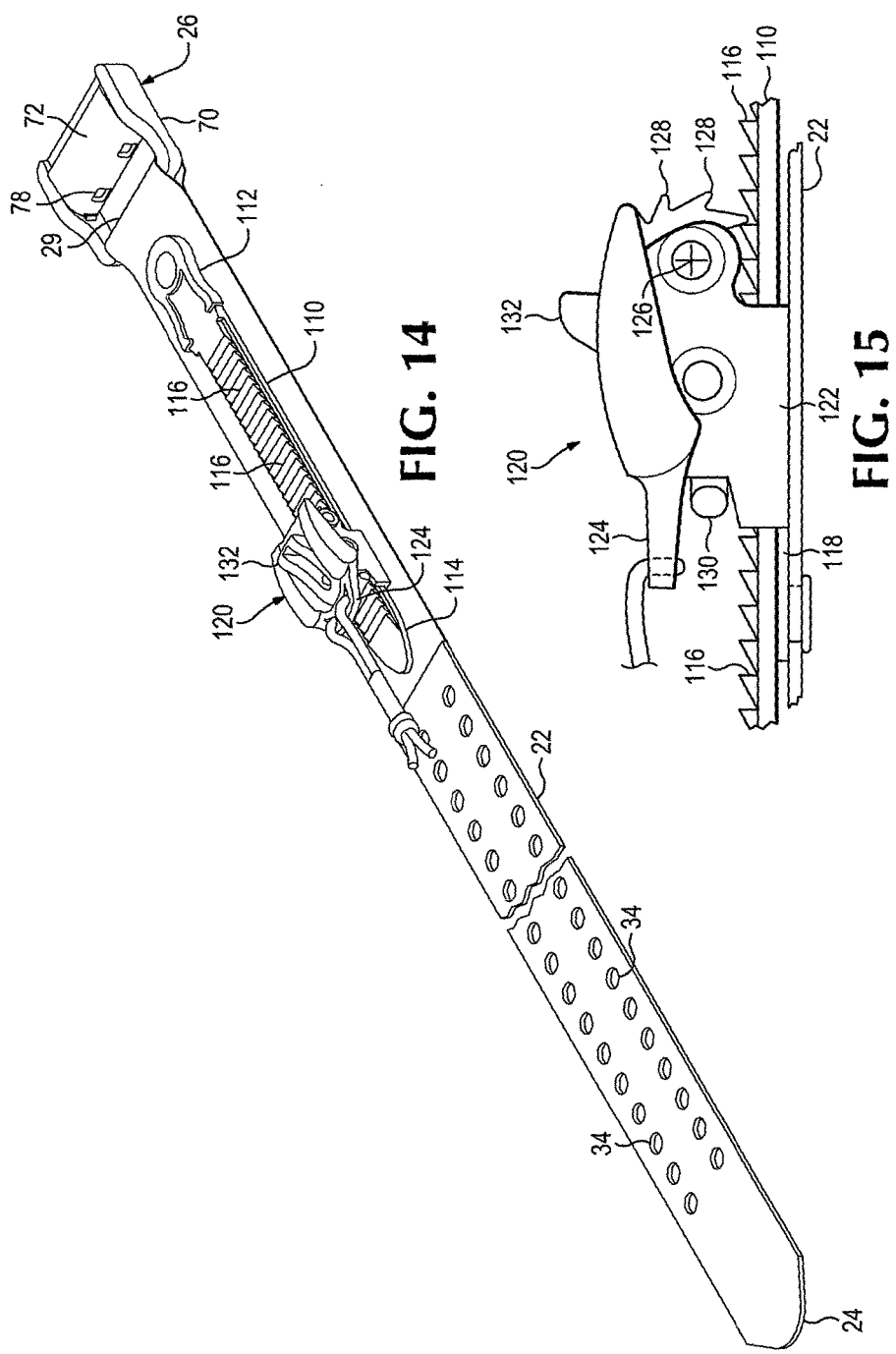

EXTREMITY TOURNIQUET

CROSS-REFERENCE TO RELATED APPLICATIONS

This application claims the benefit of the filing date of U.S. patent application Ser. No. 61/935,566, filed Feb. 4, 2014, entitled "Extremity Tourniquet."

BACKGROUND OF THE INVENTION

The present application relates to tourniquets, and particularly to emergency tourniquets intended for rapid application to a patient's limb, such as a severely injured leg or arm, to minimize or stop blood loss.

Most modern emergency tourniquets are applied by using the following three similar steps: 1) Placement: A tourniquet in the form of a loop is placed in the correct position around a wounded extremity, proximal to the injury sustained by an artery or other blood vessel. The tourniquet can either be fitted as a pre-existing closed loop, or a linear strap may be placed around the limb and then formed into a closed loop. Converting from a linear strap to closed loop is most commonly achieved by routing the strap through a buckle, or by the use of one of many other mechanisms including but not limited to a quick-release buckle already in place on the strap, or a hook-and-bar fastening arrangement.

2) Gross Circumference adjustment: A strap encircling a limb is manually pulled (usually through a buckle) to tighten the loop snugly around the extremity, removing all slack and, preferably, beginning to constrict the affected limb.

3) Fine Circumference adjustment: A mechanism is used to further tighten the loop to the point where blood flow is restricted or occluded. This mechanism is most commonly in the form of Spanish windlass, as in the CAT and SOFT-T tourniquets shown in U.S. Pat. No. 7,842,067 or 7,892,253 or may be one of many other mechanisms including but not limited to a ratchet as shown in U.S. Pat. No. 7,947,061, a string-and-pulley system, or a pneumatic system.

Three common shortfalls of available emergency tourniquets are:

1) Too much slack remains in the loop after Gross Circumference adjustment, leading to ineffectiveness of the Fine Circumference adjustment mechanism. This can result in slower application times, increased initial blood loss, or complete ineffectiveness.

2) The securement devices associated with the Gross Circumference adjustment mechanism may accidently loosen, fail, or be released after control of a hemorrhage is achieved, resulting in resumed or continued bleeding. This may be exacerbated by the fact that the Fine Circumference adjustment places an increasing force on the Gross Circumferential fastener, making the securement device more prone to failure.

3) The user is confused as to whether two tourniquets are necessary. Currently large thighs often require two tourniquets. However, the operator does not know whether a first tourniquet has too much slack in it or whether it is functioning as intended. As a result, the operator is not sure whether to remove and reapply the first one or put on a second.

SUMMARY OF THE INVENTION

An emergency extremity tourniquet and a method of applying it disclosed herein utilizes an elongate flexible strap to encircle an injured limb and a force-regulating buckle that receives the strap and engages the strap securely once a predetermined amount of tension is applied to the buckle by the strap. Thereafter, while the strap extends through the buckle, an outer end of the strap is engaged with the part encircling the limb, holding the tourniquet in place around the affected limb of the patient with a certain amount of tension in the strap, the fine adjustment of the tourniquet can be accomplished without risk of losing tension in the strap during the fine adjustment.

In one embodiment of the emergency extremity tourniquet disclosed herein an outer end of the strap may be engaged with the force-regulating buckle before the tourniquet is applied to a limb, and the force-regulating buckle may be connected quickly with the opposite end of the strap by a quick-release fastening device such as a side release buckle.

In one embodiment of the emergency extremity tourniquet disclosed herein fine adjustment of the circumference of the tourniquet is accomplished by a Spanish windlass acting on a secondary tension-bearing member associated with the strap.

In one embodiment of the emergency extremity tourniquet disclosed herein a tensioning ratchet is arranged to act between two spaced-apart points on the strap so as to reduce the circumference of the tourniquet.

In one embodiment of the emergency extremity tourniquet disclosed herein, a ratchet-equipped winding device may be used to tighten a string in a pulley-like arrangement providing a mechanical advantage to reduce the circumference of the tourniquet.

In one embodiment of the emergency extremity tourniquet disclosed herein an inflatable bladder may be used to increase radially inwardly-directed pressure on the limb on which the tourniquet has been applied.

According to the method disclosed herein, an elongate member such as a strap is placed around a limb, engaged with a force-control buckle, and manually tightened until the buckle senses a predetermined level of tension at which the buckle engages and immobilizes the strap or other elongate member, and a part of the strap extending out beyond the buckle is fastened to the part extending around the limb. Thereafter, with the strap held stationary with respect to the force-control buckle, fine circumferential adjustment is used to tighten the tourniquet further until the tourniquet effectively stops blood flow in the limb being treated.

Application of an extremity tourniquet according to the disclosure herein can provide assurance of proper constriction of a large limb such as a patient's thigh, as application of the tourniquet involves first the step of fastening an elongate member of the tourniquet around the affected limb with a predetermined amount of tension as regulated by a force-control buckle. The tension in the tourniquet is then increased by the use of a fine adjustment mechanism, and the user can determine with confidence whether a second tourniquet should be applied, as the force-controlled buckle provides assurance that a first tourniquet has been applied in a manner that assures proper function of the first tourniquet.

The foregoing and other objectives and features of the invention will be more readily understood upon consideration of the following detailed description of embodiments of the invention taken in conjunction with the accompanying drawings.

BRIEF DESCRIPTION OF THE DRAWINGS

FIG. 8 is a sectional view taken along 8-8 in FIG. 6, showing the construction of a first version of the buckle incorporating a pair of coiled springs.

FIG. 9 is a sectional view similar to FIG. 8, but showing a slightly different version of the buckle incorporating an additional spring.

FIG. 10 is a sectional detail view of an end portion of one of the strap-retaining pins of the buckle.

FIG. 11 is a view similar to that of FIG. 10 showing an end portion of a strap-retaining pin having a somewhat different configuration.

FIG. 14 is an isometric view of the emergency extremity tourniquet shown in FIG. 13 with the tourniquet extended and in a flat configuration, with the strap foreshortened so as to depict other components with greater clarity and at an enlarged scale.

FIG. 15 is a detail view of the ratchet mechanism shown as part of the tourniquet illustrated in FIGS. 13 and 14.

DETAILED DESCRIPTION OF PREFERRED EMBODIMENTS

Figure 1:
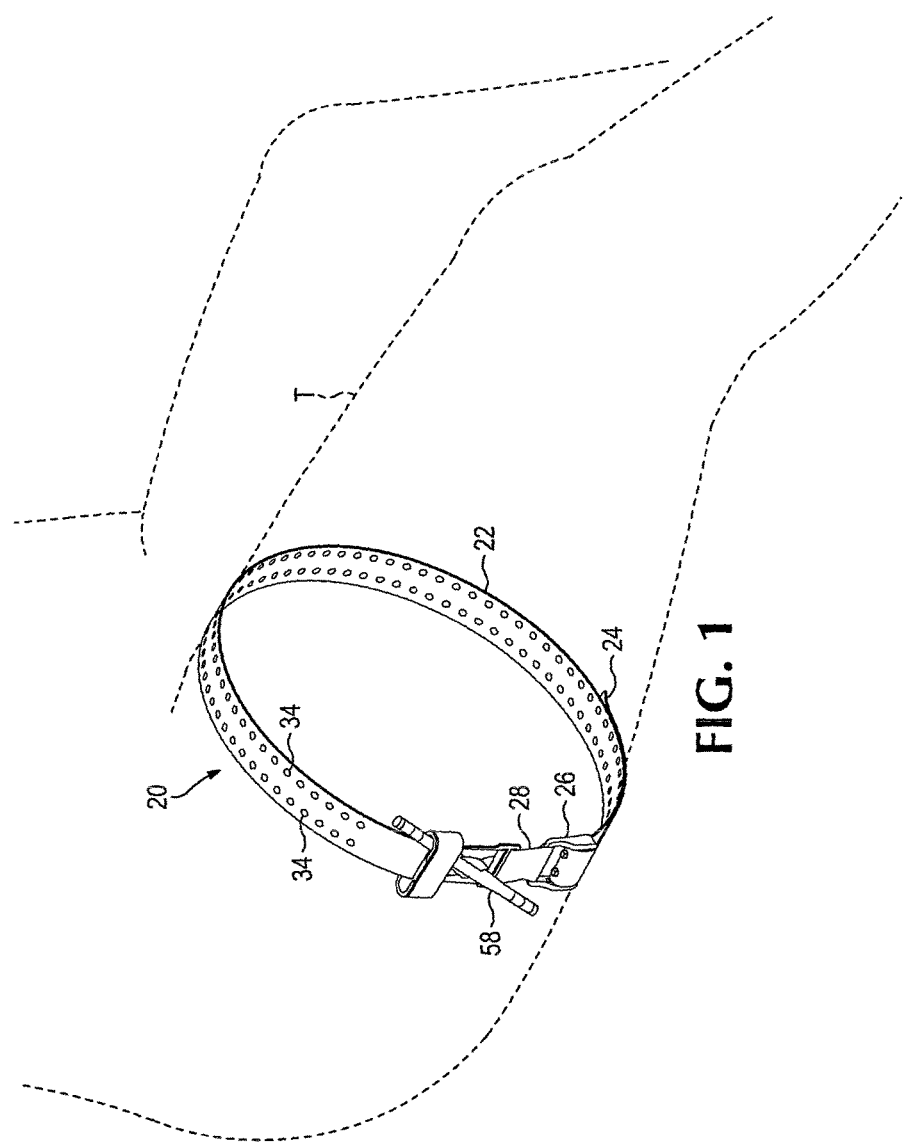
FIG. 1 is an isometric view of an extremity tourniquet attached to a person's thigh, shown in broken line.
Figure 2:
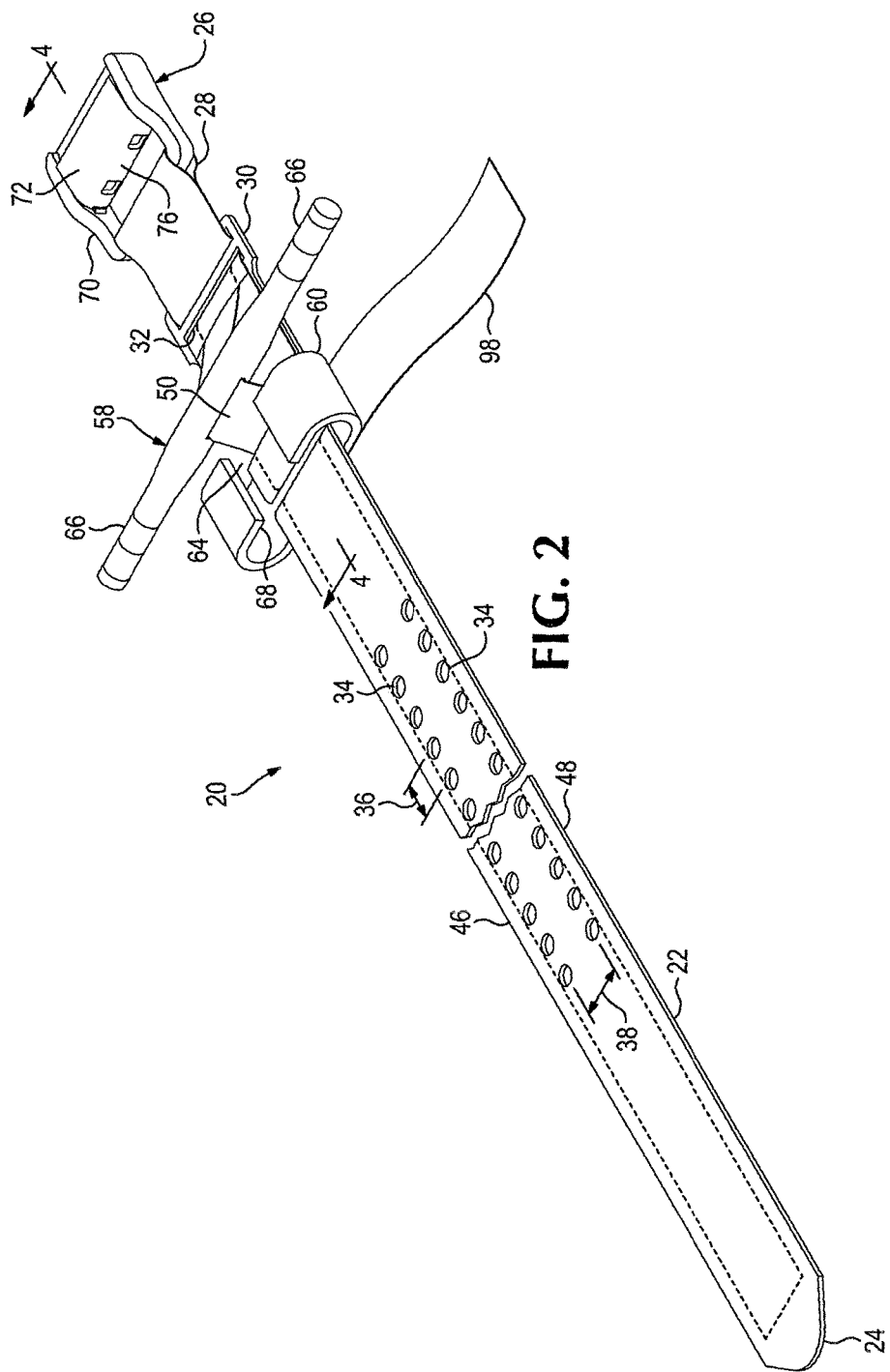
FIG. 2 is an isometric view of the tourniquet shown in FIG. 1, with the tourniquet extended in a straight and flat configuration, showing the main strap of the tourniquet foreshortened, to depict other components of the tourniquet with improved clarity at an enlarged scale.
Figure 3:
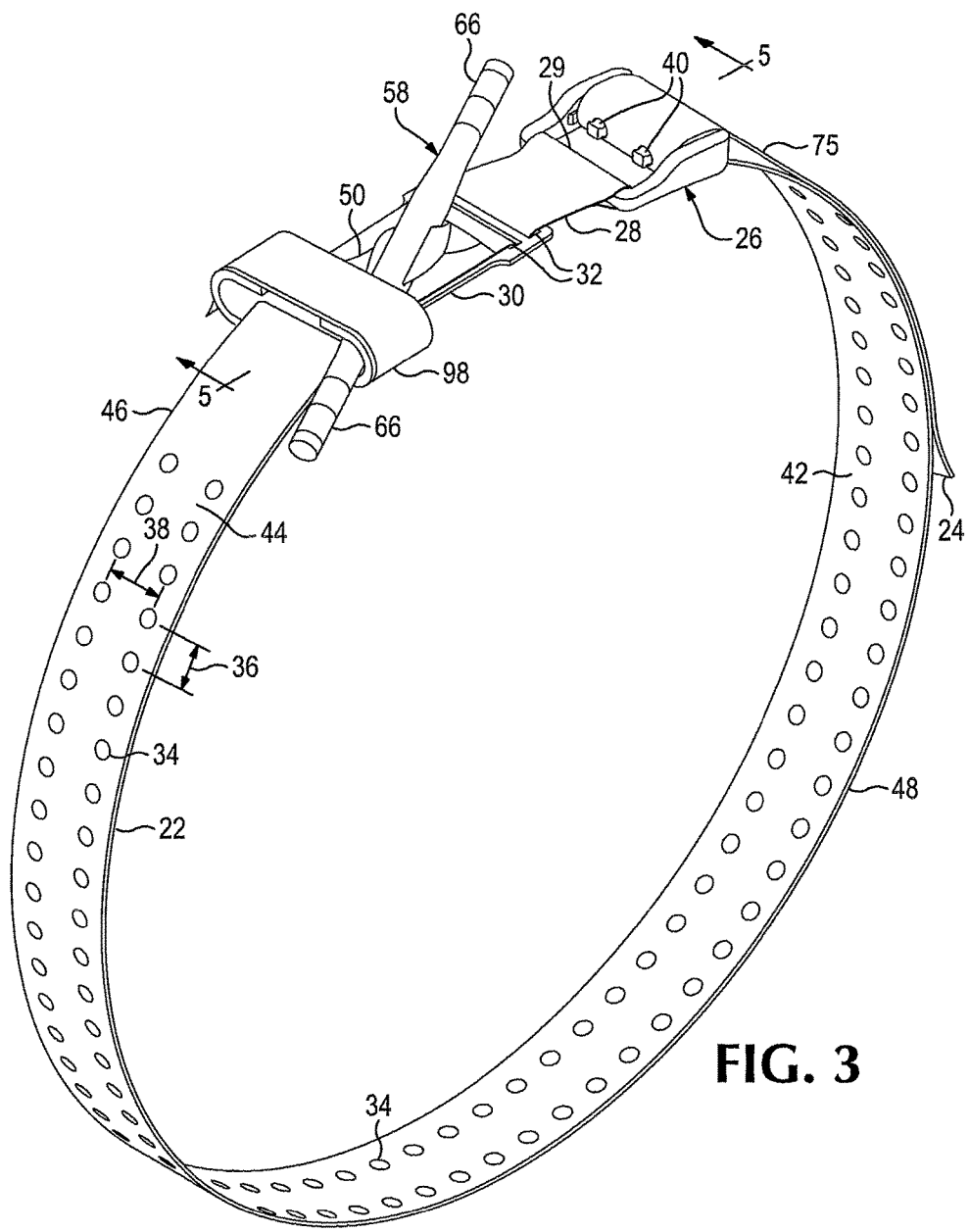
FIG. 3 is an isometric view of the tourniquet shown in FIGS. 1 and 2, showing the tourniquet in the configuration in which it is used on a patient.
Figure 4:
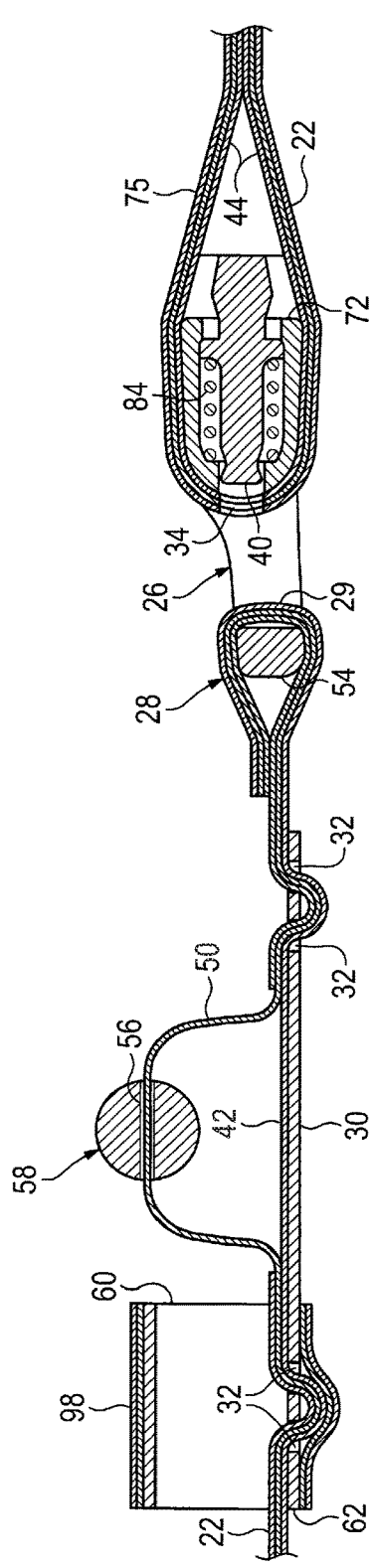
FIG. 4 is a sectional view taken along line 4-4 in FIG. 2, but showing the condition of the secondary tightening mechanism prior to final tightening of the tourniquet.
Figure 5:
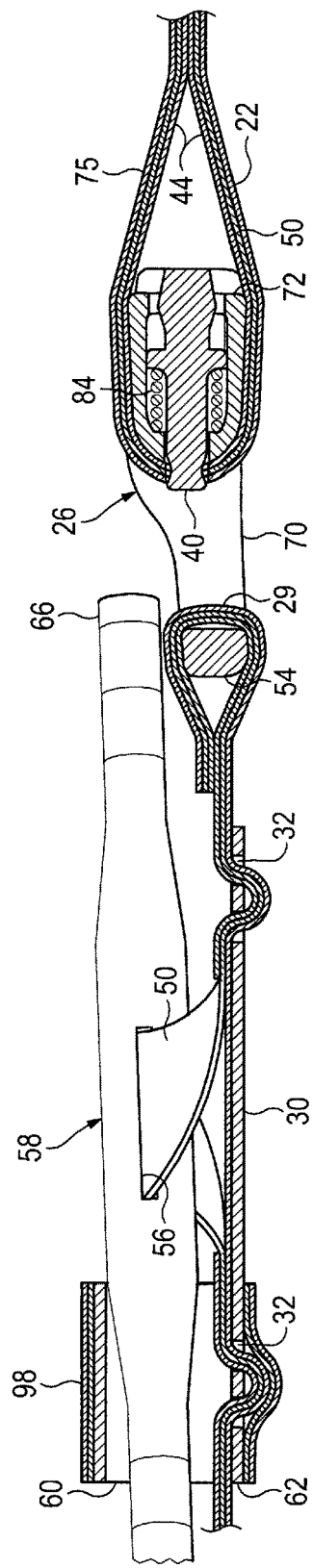
FIG. 5 is a sectional view similar to FIG. 4, taken along line 5-5 in FIG. 3, showing the manner in which the tourniquet is retained in a final tightened condition.

Referring to the drawings that form a part of the disclosure herein, a tourniquet 20 which is a first embodiment of the emergency extremity tourniquet disclosed herein is shown in FIGS. 1-9. In FIG. 1, the tourniquet 20 is shown in place on a patient's thigh T. As shown somewhat more clearly in FIGS. 2 and 3, the tourniquet 20 includes an elongate strap 22 having a first, or outer, end 24 and a buckle 26 attached to its opposite, second, end 28 as by a loop 29 around a part of the buckle 26. A backing plate 30, of a suitably strong plastic resin or of sheet metal, for example, may be provided, and the strap 22 may be threaded through a pair of slots 32 provided at each end of the backing plate 30, as shown in FIGS. 4 and 5.

The strap 22, as may be seen in FIGS. 1-3, includes an array of pairs of holes 34 spaced apart from each other along the length of the strap by a distance 36. The holes 34 are spaced apart from each other laterally of the strap 22 by a distance 38 corresponding to the spacing between a pair of pins 40 of the buckle 26, and each of the holes 34 is large enough to receive one of the pins 40 comfortably. For example, the longitudinal center-to-center distance 36 may be about 0.75 inch, and the lateral center-to-center distance 38 may be about 1.0 inch.

The strap 22 may be constructed of two outer layers of strong, flexible, non-elastic fabric, a first layer 42 and a second layer 44 that may be faced with a self-engaging fastening material such as OMNI-TAPE® Velcro® or other material or devices that will secure confronting parts of the layer 44 to each other to prevent relative movement. The two layers 42 and 44 may be sewn or otherwise securely attached to each other, as by gluing, stapling, clamping, thermally welding or ultrasonically welding them together along their parallel opposite margins 46 and 48 and at the outer end 24. It will be understood that the strap 22 may also be formed of a wider piece of such fabric folded over to form one longitudinal edge and with a pair of laterally opposite longitudinal margins of the material fastened together as the other longitudinal edge of the strap 22.

Between the first layer 42 and second layer 44 there may be a strong, flexible, elongate member 50 that may be ribbon-like securely attached to the outer layers 42 and 44 only at the outer end 24 and extending longitudinally between the layers 42 and 44 to the opposite end 28 of the strap 22. As shown in FIGS. 4 and 5, the ribbon-like member 50 may be a single member with an end 52 attached to the outer members 42 and 44 at the outer end 24 of the strap 22, but it would also be possible for it to be provided in the form of a loop extending along the entire length of the strap 22, with both ends 52 of the ribbon-like member 50 attached securely within the strap 22 at the outer end 24, and a mid-length part of the ribbon-like member 50 included in the loop 29 extending around the bar 54 of the buckle 26, as shown in FIGS. 4 and 5. The ribbon-like member 50 is preferably wide enough to have ample strength and may extend laterally beyond both of the holes 34 of each pair, so that the holes 34 extend entirely through the layers 42 and 44 and may also go through the ribbon-like member 50, yet it needs to be narrow enough to lie flat between the layers 42 and 44 of the strap 22. The ribbon-like member 50 is free to slide longitudinally between the layers 42 and 44 except for having its ends fastened, and except when holes in the ribbon-like member 50 are engaged by the pins 40. In the latter case, the portion between the pins 40 and the near end 28 of the strap 22 remains free.

The ribbon-like member 50 also extends through an aperture such as a slot 56 defined by and extending through a mid-length part of a rod-shaped winding member 58 located adjacent the backing plate 30 as shown best in FIGS. 4 and 5 where a portion of the ribbon-like member 50 is depicted with exaggerated length for the sake of clarity. Preferably, the length of the ribbon-like member 50 is similar to that of the outer layers 42 and 44, so that the ribbon-like member 50 ordinarily lies closely alongside the layer 42 of the strap 22. The layer 44 of the strap 22 may be interrupted near an end of the backing plate 30 to expose the ribbon-like member 50 between the pairs of slots 32 in the backing plate member 30. The winding member 58 can be utilized as a Spanish windlass to twist and wind the ribbon-like member 50 and thus effectively shorten the ribbon-like member 50, at least between the buckle 26 and the loop 29, to tighten the tourniquet further after a baseline amount of tension has been established. A retainer 60 may be attached to or may be formed as an integral part of an end 62 of the backing plate 30. The retainer 60 is oriented transversely with respect to the strap 22, with an open space 64 between opposite ends of the retainer 60, and each end is in the form of a C-shaped hook 68 large enough to receive and hold one of the opposite ends 66 of the winding member 58.

The buckle 26 is a force-regulating buckle that cooperates with the strap 22 by engaging the pins 40 in a respective pair of the holes 34 spaced apart from each other along the length of the strap 22 when a predetermined amount of tension in the strap 22 is applied to the buckle 26. as shown in FIGS. 6 through 11, the buckle 26 may include two main parts, a rigid frame 70, and a sliding block 72. A bar 54 at an inner end of the frame 70 is secured to the second end portion 28 of the strap 22 by the small loop 29 of the fabric of the strap 22, including the ribbon-like member 50. The outer end portion 75 of the strap 22 may extend through the opening defined by the frame 70, as shown best in FIGS. 4 and 5, sliding along a contact surface of the curved face 76 of the sliding block 72. A pair of holes 78 are defined in the sliding block 72, and the pins 40 extend from the frame 70 into the holes 78, with their ends preferably below or flush with the face 76 when the buckle 26 is not in tension.

The tourniquet is applied to a person's injured limb by first placing the strap 22 around the limb proximal to a hemorrhage-causing or bleeding injury, and the outer end 24 of the strap is then threaded outward through the opening of the buckle 26. The outer end 24 is doubled back around the curved face 76 and pulled through the buckle 26 so as to reduce the size of the main loop of the strap 22 around the limb until the tension in the main loop is sufficient to move the sliding block 72 to the right, as indicated by the arrow 74 and as seen in FIGS. 2 and 3, toward the position shown in FIG. 7A, relative to the frame 70 of the buckle 26, and the pins 40 can extend into a pair of holes 34, thus engaging the strap 22, and preventing it from moving relative to the buckle 26, apart from any differences in size between the pins 40 and the holes 34. The holes 34 in the strap 22 may have a slightly larger diameter than the largest transverse dimension of each of the pins 40, so that engagement of the pins 40 in the holes 34 occurs easily and smoothly at the desired tension in the strap 22. The user then presses the outwardly extending pulled part 75 of the strap 22 located near the buckle 26 against the exterior of the main loop so that the fastener surfaces on the layer 44 of the strap 22 engage one another, or such other fastening material or devices that are provided are activated, to prevent the part 75 of the strap extending outward beyond the buckle 26 from moving relative to the portion of the strap 22 forming the main loop around the injured limb to retain the strap 22 at the desired location with respect to the sliding block 72.

Thus, in the gross circumference adjustment phase of applying the emergency terminal tourniquet 20, holes 34 in the strap 22 are engaged, and holes in the ribbon-like member 50, if present, may be engaged by the prongs, or pins, 40 of the buckle 26 once a predetermined baseline level of tension is reached in the strap 22. It will be appreciated that a closer longitudinal spacing distance 36 between holes 34 should provide greater accuracy of the baseline tension.

When the strap 22 is engaged in the buckle 26 and placed in sufficient tension against the curved face 76, once a pair of holes 34 in the strap 22 move into alignment with the holes 78 in the sliding block 72 the tension in the strap 22 moves the sliding block 72 so that the pins 40 protrude from the holes 78.

Figure 6:
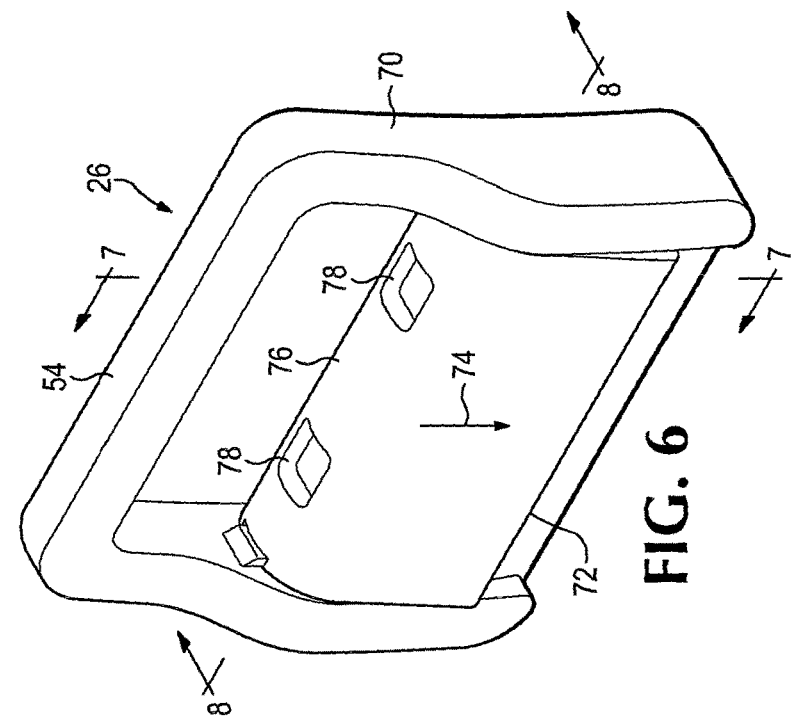
FIG. 6 is an isometric view of a force-regulating buckle such as that incorporated in the tourniquet illustrated in FIGS. 1-5.

FIGS. 4 and 5 show a spring 84 positioned around one of the pins 40. An identical spring 84 may be used on the other pin 40, as shown in FIG. 8, and there may be three springs 84, as shown in FIG. 9, if desired to assure greater tension in the tourniquet 20. The springs 84 are compressed somewhat when the sliding block 72 is in its fully extended position, as shown in FIGS. 4, 6, and 7A, so that some force must be applied to the buckle 26 by tension in the strap 22 before the sliding block 72 begins to move relative to the buckle frame 70. The internal springs 84 are compressed further as the sliding block 72 moves right, toward the position shown in FIGS. 5 and 7B, when there is sufficient tension in the strap 22.

Flanges 92 on the buckle frame 70 are engaged by lips 94 on the sliding block 72 when the buckle 26 is not in tension and the sliding block 72 is in the fully extended position as shown in FIGS. 4 and 6, thus withstanding the compressive force in the springs 84.

As the sliding block 72 moves rightward toward the position shown in FIG. 3 from the position shown in FIG. 2 and FIG. 6, the lips 94 ride up and over the tops of the ramps 96 beneath the flanges 92, so that movement of the sliding block 72 may create an audible click as the sliding block 72 moves relative to the frame 70 and the pins 40 extend into the holes 34, indicating to the user that the buckle 26 is engaged with the strap 22. Thereafter the inwardly directed elastic force in the sides of the sliding block 72 presses the lips 94 against the ramps 96 and helps keep the sliding block 72 in its depressed position, to keep the pins 40 engaged in the holes 34. A slightly lower amount of tension in the main loop of the tourniquet 20 between the pins 40 and the loop 29 is then sufficient to keep the sliding block 72 in the rightwardly depressed position, once the pins 40 have become engaged in the holes 34 as shown in FIGS. 3 and 5.

Thus, when the proper initial amount of tension as determined by the springs 84 in the buckle 26 has been reached in the main loop portion of the emergency terminal tourniquet 20 wrapped around an injured limb of a patient, the pins 40 of the buckle 26 will engage the strap 22, and so long as tension in the main loop portion of the strap 22 extending from the bar 54 of the buckle 26 and around the limb is not more than slightly reduced, the pins 40 will remain engaged in the holes 34. It will be understood that the buckle 26 could be constructed to include only one pin 40 or more than two pins 40 and that the strap 22 could be provided with compatibly located holes 34.

Figure 7B:
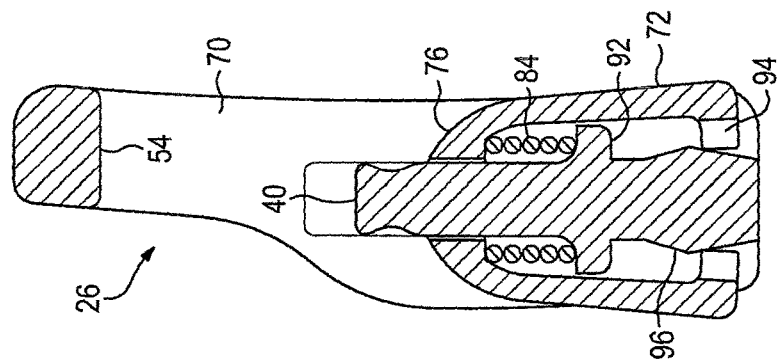
FIG. 7B is a view similar to FIG. 7A, but showing the condition of the buckle when the strap portion of the tourniquet is under tension, as with the tourniquet in use as shown in FIG. 1.
Figure 7A:
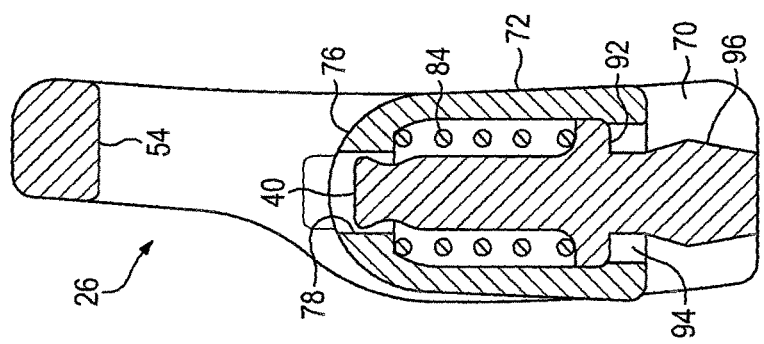
FIG. 7A is a sectional view taken along line 7-7 in FIG. 6 showing the buckle in the condition in which it is illustrated in FIG. 6.

Referring to FIGS. 10 and 11, the pins 40 of the buckle 26 may have outer tips shaped as shown in FIGS. 7A and 7B, with a shallow groove 80 extending around each pin near its tip, as shown in FIG. 10. Alternatively, as shown in FIG. 11, a shallow groove 82 may extend partially around the tip of a pin 40' on only the side against which a hole 34 would pull when the strap 22 is under tension. The groove 82 thus would be on the upper side of a pin 40' oriented as illustrated in FIG. 3 wherein the main loop of strap 22 of the tourniquet is pulling in a primarily downward direction as illustrated in FIG. 3.

The mated fastener material on the layer 44 will hold the strap 22 engaged with the buckle 26 at the location where the pins 40 of the buckle 26 are engaged in a pair of holes 34 along the strap 22. Accordingly, engagement of the fastener material maintains sufficient tension in the outer, or pulled, free portion 75 of the strap 22 to keep the pins 40 of the buckle 26 engaged in a pair of holes 40 in the strap 22, to maintain a consistent predetermined initial application, or baseline, amount of tension, in the tourniquet 20. The baseline tension may acceptably be in the range of about six pounds to about 33 pounds, and a baseline tension of about 18 pounds has been found to be satisfactory, in that it allows tension to be increased sufficiently without exceeding the range of adjustment available. As shown in FIGS. 1 and 3, the effective circumference of the emergency terminal tourniquet is thus maintained at an initial size providing compression of an injured limb, as a reliable basis with a known baseline tension for additional fine circumferential tightening of the emergency extremity tourniquet 20 to achieve termination of hemorrhaging.

With the emergency extremity tourniquet 20 in place on a patient's injured limb with the strap 22 engaged with the buckle 26 so as to provide the predetermined baseline amount of tension, further tightening of the tourniquet 20 can be provided by utilizing an included fine adjustment mechanism. As shown in FIGS. 1 through 5, a winding member 58 can be used as a Spanish windlass to tighten the ribbon-like member 50. Turning the winding member 58 as shown in FIGS. 3 and 5 shortens the portion of the ribbon-like member 50 between the layers 42 and 44 of the strap 22, at least between the pins 40 and the bar 54 of the buckle 26, further tightening the tourniquet 20 around the injured limb, while leaving the outer layers 42 and 44 of the strap 22 in place, albeit with reduced tension. Once bleeding from an open wound or other evidence of hemorrhage in a distal portion of the patient's limb has been terminated, one of the end portions 66 of the winding member 58 can be engaged in one of the hooks 68 of the retainer 60 to prevent unwinding of the ribbon-like member 50 and maintain the increased tension in the tourniquet 20.

A retainer strap 98 can then be applied to surround the retainer 60. The retainer strap 98 can held in place by a suitable fastener such as a pressure-sensitive adhesive, hook-and-loop fastener material, snaps, or another device. Preferably, the retainer strap 98 has an outer surface that can readily receive and legibly retain information written with a normally available writing instrument, so that the time of application of the tourniquet 20, for example, can be recorded for the use of medical personnel at a later time as when the tourniquet 20 has been applied during triage.

Consistent baseline tension as provided by tightening the strap 22 until the buckle 26 operates as described above means less fine circumference adjustment is needed, and that the amount of such fine adjustment may be more consistent than when the needed initial tension in a tourniquet is simply estimated by the user. Fewer Spanish windlass turns results in faster tourniquet application, and less variation user to user and patient to patient. A more consistent required number of windlass turns results in easier user training and more intuitive use of a tourniquet capable of providing such a predetermined amount of baseline tension.

When the tourniquet 20 is first applied under baseline tension and the free portion 75 of the strap 22 is secured, the prongs or pins 40 may or may not later retract (as when the tension diminishes slightly through tissue or textile relaxation). As the Spanish windlass is tightened, the prongs or pins 40 protrude again and positively engage the holes 34. The tourniquet 20 cannot be removed thereafter without unwinding the Spanish windlass. In other words, as the fine circumference adjustment force is increased, the risk of the tourniquet loosening or becoming detached decreases.

Figure 12:
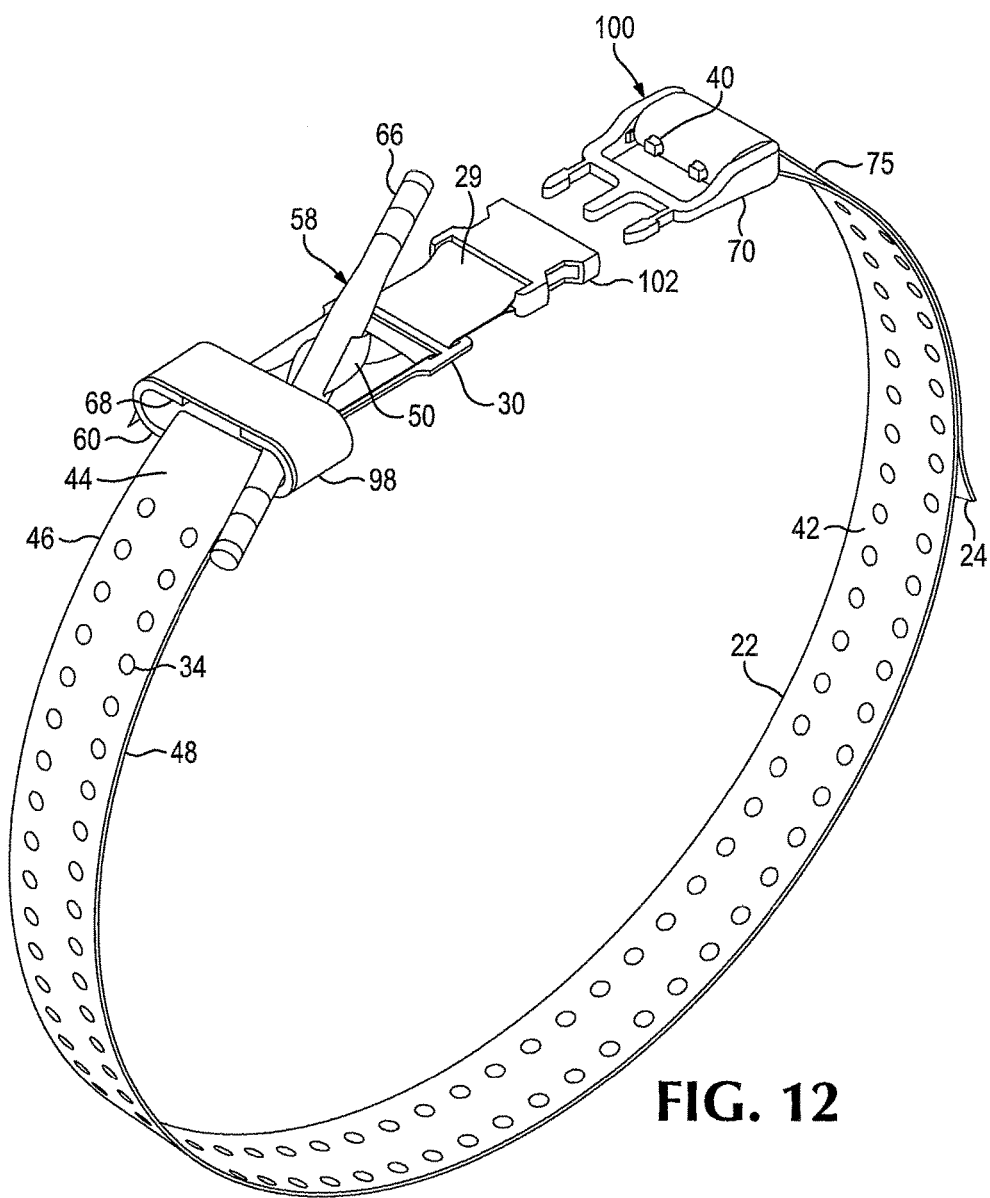
FIG. 12 is a view similar to a portion of FIG. 3, showing another version of the emergency extremity tourniquet disclosed herein, in which the force-regulating buckle is attached to the strap in a different manner.

As shown in FIG. 12, a force-regulating buckle 100, similar to the buckle 26, may be attached to the second, or inner, end 28 of the strap 22 so as to be separated easily from it. As a benefit of this possibility, the outer end 24 and adjacent part 75 of the strap 22 can be threaded through the buckle 100, with the parts of the strap 22 held together and immobilized with respect to each other by the fastening material on the outer layer 44, and thus kept ready for quick initial application. For example, the female part of a side release buckle 102 may be attached to the inner end 28 of the strap and the force-regulating buckle 100 can be connected to or disconnected from the inner end 28 of the strap by operation of the side release buckle 102. Application of the tourniquet 20 to a patient may then be accomplished simply by fastening the side release buckle, resulting in the outer end free portion 75 of the strap being immediately available to tighten the main loop of the tourniquet 20 around the patient's limb until the force-regulating buckle 100 detects sufficient baseline tension present in the loop and engages its pins 40 into the holes 34 in the strap 22. Instead of a side release buckle, other easily connected arrangements, such as a hook and a loop, may be used to attach the buckle to the inner end 28 of the strap 22.

The beneficial effects of using the force-regulating buckle 26 or 100 can also be obtained in the emergency extremity tourniquet 20 using other mechanisms for fine circumference adjustment, as shown in FIGS. 13 through 19.

Figure 13:
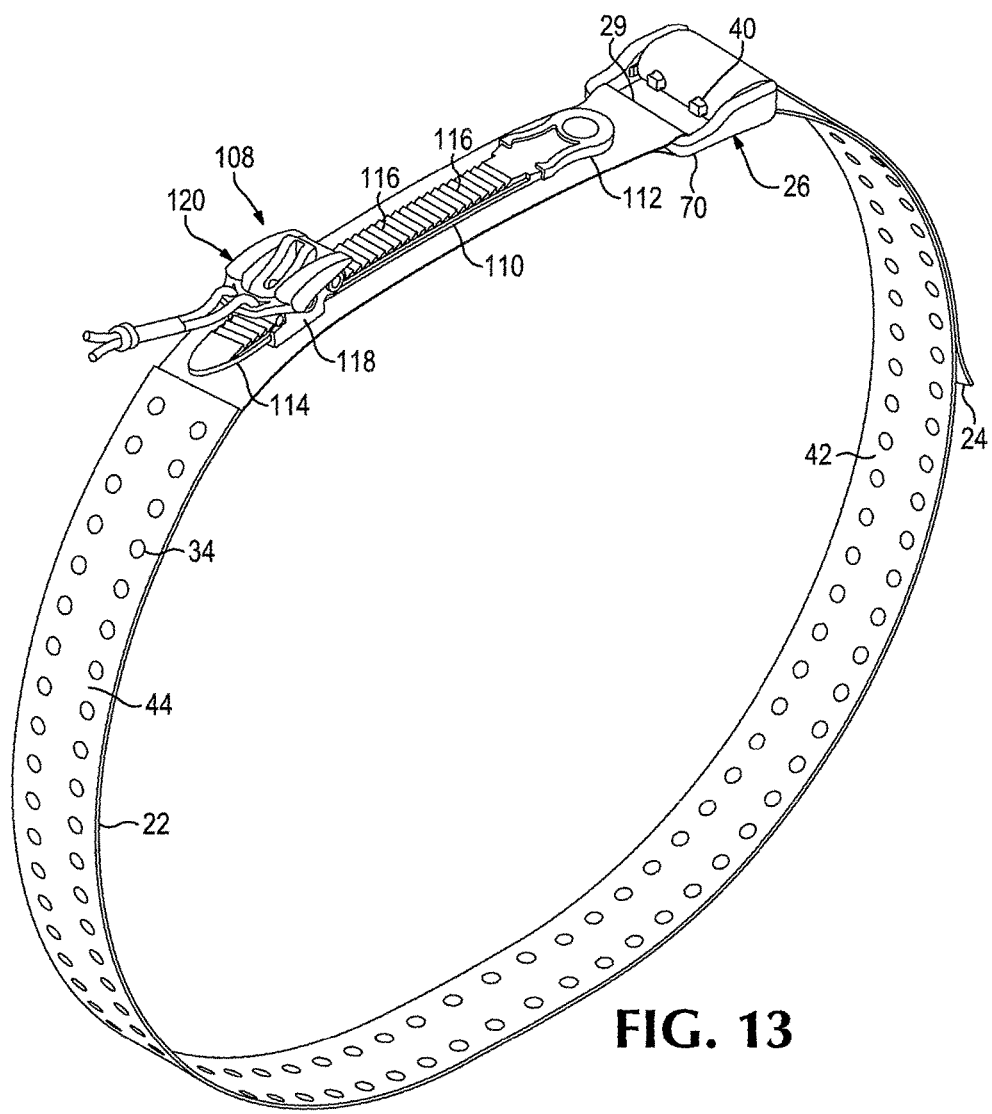
FIG. 13 is a view similar to a portion of FIG. 3, showing another version of the emergency extremity tourniquet disclosed herein, in which fine adjustment is accomplished by use of a ratchet device.

In particular, in a tourniquet 220 shown in FIGS. 13-15 a ratcheting assembly 108 may include an elongated, toothed ratchet tongue 110 having an inner end 112 attached to the inner end 28 of the strap 22, a short distance from the loop 29 by which the buckle 26 or a side release buckle 102 is attached. The ratchet tongue 110 extends along the strap 22 to an outer end 114 of the ratchet tongue, and an array of ratchet teeth 116 are provided along the ratchet tongue 110. Aligned with the outer end 114 of the ratchet tongue and fastened securely to the strap 22 is a mounting base 118 carrying a lever-operated ratchet mechanism 120. A body 122 of the lever-operated ratchet mechanism defines a passageway through which the ratchet tongue 110 extends movably, and a lever 124 mounted on the body can be pivoted about an axis 126, to move lever teeth 128 into engagement with successive ones of the ratchet teeth 116 and thus to pull the ratchet tongue 110 through the body 122. A spring-loaded retaining pawl 130 keeps ratchet tongue 110 from moving back out of the ratchet body 122 as the ratchet lever 124 is returned to its original position to disengage the lever teeth 128 and permit them to engage other ratchet teeth 116 further along the ratchet tongue 110. The pawl 120 may be released by pulling on a release lever 132 when it is desired to release the tourniquet 20.

Figure 16:
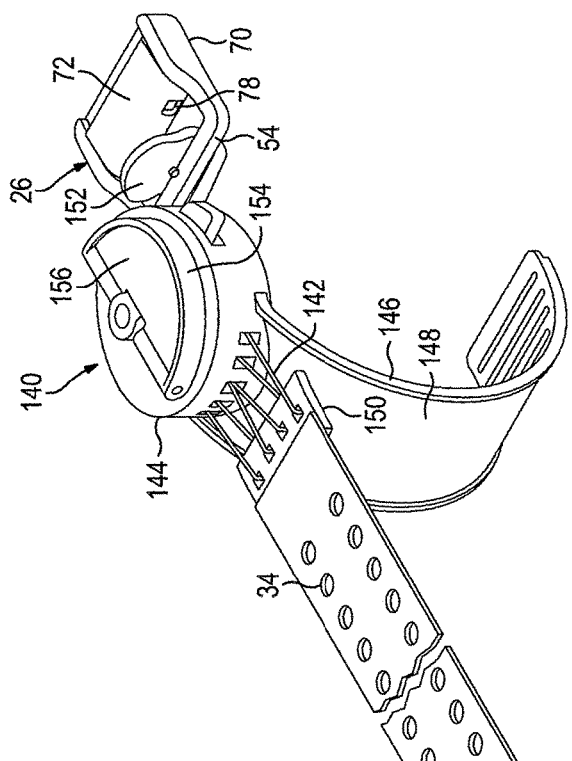
FIG. 16 is a view similar to a portion of FIG. 3, showing another version of the emergency extremity tourniquet disclosed herein, in which fine adjustment is accomplished by use of a string-and-pulley device.
Figure 17:
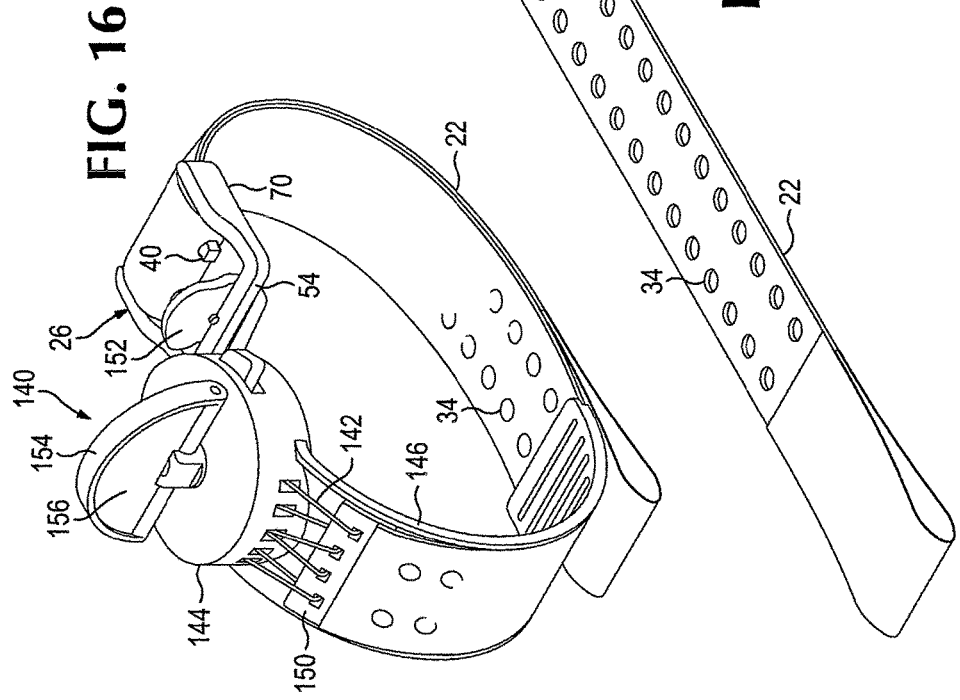
FIG. 17 is a detail view showing the fine adjustment device shown in FIG. 16 at an enlarged scale.

Fine circumferential adjustment of an emergency terminal tourniquet 320 may also be accomplished, as shown in FIGS. 16 and 17, by a tensioning mechanism 140 in which a strong cord or string 142, which may be similar to braided fishing line, of a strong artificial fiber such as Dacron®, for example, may be tightened by a winding mechanism 144 including a spool held by a ratchet. The string may extend from the winding mechanism 144 to the inner end 150 of the strap 22 and be arranged to extend back and forth through several holes to give a mechanical advantage as the string 142 is wound. The winding mechanism 144 may be held in a winder body from which a guide strap 146 extends toward and within a main guide channel 148 along part of the loop formed by the strap 22, as shown with the extremity tourniquet 320 in place upon a patient's limb, in FIG. 16. Thus, tightening the string 142 moves the second, or inner, end 150 of the strap 22 toward the winding mechanism 144. At a side of the winding mechanism opposite the location of the cord, the force-regulating buckle may be attached to the winding mechanism body, either removably, as by a hook 152 engaging the bar 54 of the frame 70 of the force-regulating buckle 26, or, by a more permanent connector (not shown) extending from the winding mechanism 144 to the frame of the force-regulating buckle 26. A winding handle 154 may be attached to a spool shaft of the winding mechanism 144 in a manner allowing the winding handle 154 to be folded flat against a top of the winder mechanism 144, and the winder handle may include a surface 156 on which information can be recorded regarding the identity of the patient and the time of application of the tourniquet.

Figure 18:
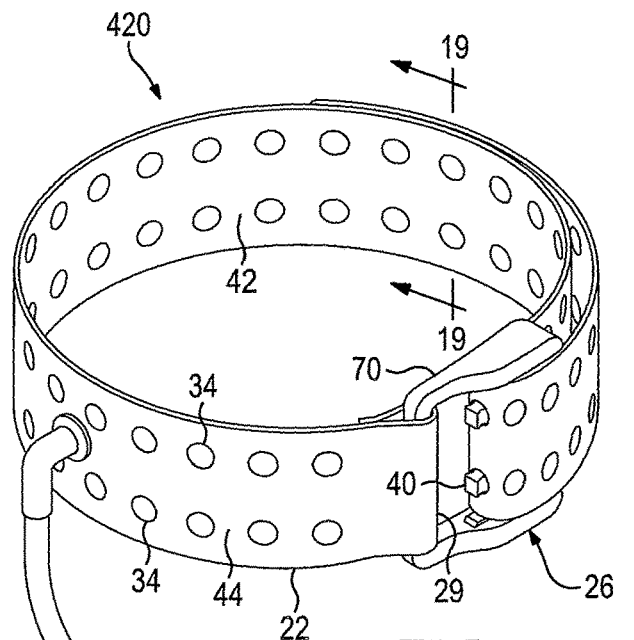
FIG. 18 is a view similar to a portion of FIG. 3, showing another version of the emergency extremity tourniquet disclosed herein, in which fine adjustment may be accomplished by the use of an inflatable bladder associated with the strap portion of the tourniquet.
Figure 19:
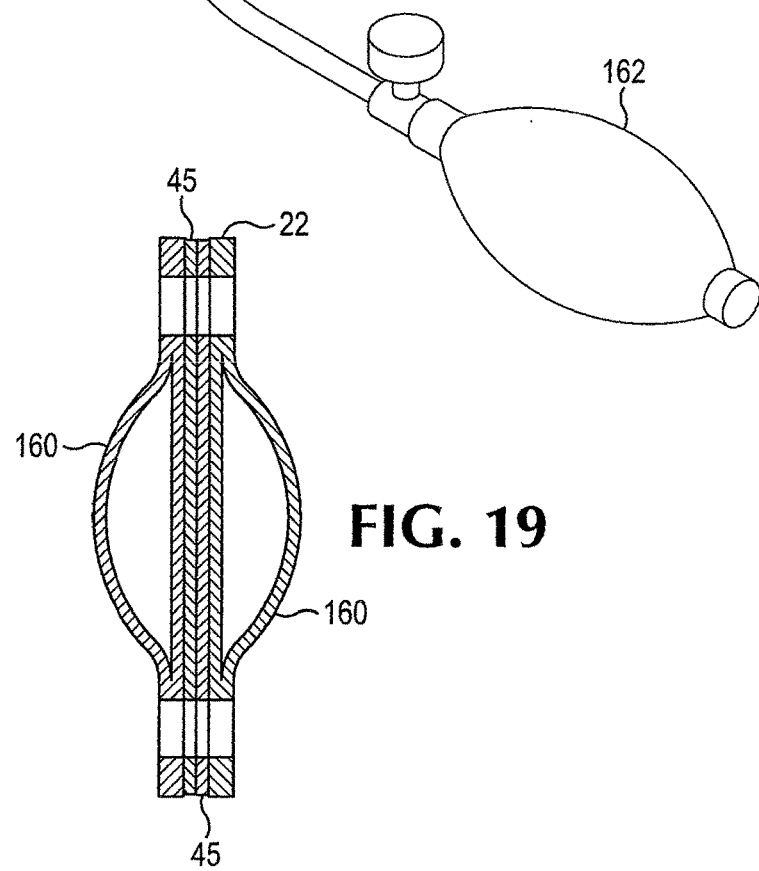
FIG. 19 is a partially cutaway view taken in the direction of line 19-19 in FIG. 18.

As another mechanism for providing fine circumference adjustment, a similar emergency extremity tourniquet 420 includes an inflatable bladder 160, as shown in FIGS. 18 and 19, that may be incorporated in or attached to the strap 22 near its inner end 28. A layer 45 of self-engaging fastener material may be provided on the second, or outer, layer 44 of the strap 22. Once the emergency extremity tourniquet 420 is initially applied to the patient's limb, with the force-regulating buckle 26 engaging holes 24 in the strap to establish the baseline tension, and the strap has been secured against movement through the buckle 26 by the layer 45 of fastener material, the bladder 160 may be inflated, using a suitable hand pump 162 or other source of pressurized air (not shown), until the effective internal circumference of the tourniquet 420 has been reduced sufficiently to stanch the hemorrhage.

Where an injury to, for example a lower leg, requires application of a tourniquet to a patient's thigh to stop bleeding, application of the emergency extremity tourniquet 20 disclosed herein gives an emergency caregiver confidence that a baseline tension in the tourniquet has been achieved. Thus, if use of the Spanish windlass winding member 58 or other fine circumference adjustment tension-increasing mechanism doesn't stop the bleeding, it is clearly because a second tourniquet is necessary and not because the first tourniquet 20 needs to be removed and reapplied.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A device for occluding hemorrhage in an extremity of a person's limb comprising:
   an elongate flexible tension-bearing member arranged to be formed into a loop around the person's limb;
   a buckle comprising
      a force-measuring mechanism arranged to sense tension in the tension-bearing member in the loop and determine when said tension has reached a predetermined baseline amount of tension that is less than an effective tension for occluding hemorrhage in the person's limb, and
      a first fastening mechanism associated with and responsive to the force-measuring mechanism and arranged to engage and retain the tension-bearing member and thus maintain the baseline amount of tension in the tension-bearing member in the loop, in response to the force-measuring mechanism determining that said predetermined baseline amount of tension has been reached in the tension-bearing member in the loop; and
      a tension-increasing mechanism, operable when said predetermined baseline amount of tension has been reached and is being maintained in the loop by the first fastening mechanism, arranged to tighten the loop and increase tension in the loop above said predetermined baseline amount of tension to produce a desired amount of tension that is greater than the baseline amount of tension for occluding hemorrhage in the person's limb.

2. The device of claim 1 including a second fastening mechanism associated with the tension-increasing mechanism and arranged to retain a status of increased tension established by the tension-increasing mechanism, once the desired amount of tension greater than the baseline amount of tension has been attained in the loop.

3. The device of claim 1 wherein the tension-bearing member includes a strap, wherein there are a plurality of holes spaced apart from one another along a length of the strap, and wherein the buckle includes, as a part of the first fastening mechanism, a pin arranged to engage one of the plurality of holes only after the baseline tension has been attained, so that engagement of the pin in the one of the plurality of holes maintains the baseline amount of tension in the tension-bearing member in the loop before operation of the tension-increasing mechanism.

4. The device of claim 1 wherein the tension-bearing member includes a strap and the buckle is permanently attached to an end of the strap.

5. The device of claim 1 including a quick-release connector attached to an end of the tension-bearing member and wherein the buckle is releasably connected to the quick-release connector.

6. The device of claim 1 wherein the tension-bearing member includes a strap that defines at least one hole and the force-measuring mechanism includes a base portion and a slide portion and has at least one pin projecting from the base portion, the slide portion having a contact surface and being mounted over the at least one pin and being movable relative to the base portion, and the slide portion being spring-biased toward a non-engaging position in which the at least one pin does not project beyond the contact surface of the slide portion, and the slide portion remaining in the non-engaging position until tension in the strap applies sufficient force to the slide portion to move the slide portion toward the base portion far enough for the at least one pin to project beyond the contact surface of the slide portion and engage said at least one hole in the strap, the pin thereby functioning as the first fastening mechanism by establishing a position of the strap with respect to the buckle and thus maintaining the baseline amount of tension in the loop.

7. The device of claim 1 wherein the tension-increasing mechanism is a Spanish windlass acting on a length of material having a pair of opposite ends attached to the tension-bearing member at locations spaced apart from each other along the length of the tension-bearing member.

8. The device of claim 1 wherein the tension-increasing mechanism acts to reduce the size of the loop around the person's limb and increase the security of attachment of the device around the person's limb.

9. The device of claim 1 wherein the tension-increasing mechanism includes an auxiliary strap connected with the tension-bearing member, a ratchet, a latch operable in conjunction with the ratchet and a lever operable in conjunction with the latch to increase tension, and a pawl operable together with the ratchet to hold and retain tension in the auxiliary strap.

10. The device of claim 1 wherein the tension-increasing mechanism includes a second flexible tension-bearing member, a flexible cord, and a winding mechanism including a ratchet arranged to maintain tension in the cord, the tension-increasing mechanism having a pair of opposite ends, one of the opposite ends being connected to a respective location on the tension bearing member of the device near a first end of the device.

11. The device of claim 1 wherein the tension-increasing mechanism includes an inflatable bladder associated with the flexible tension-bearing member and located so as to be retained within the loop when the tension-bearing member is in place around the person's limb, whereby inflating the bladder causes the bladder to occupy a portion of a space encircled by the loop and thereby increases tension in the loop and acts to help occlude a blood vessel in the person's limb.

12. The device of claim 1 wherein the first fastening mechanism includes an area of flexible fastener material carried on the flexible tension-bearing member.

* * * * *